(12) United States Patent
Leblond et al.

(10) Patent No.: US 8,243,283 B2
(45) Date of Patent: Aug. 14, 2012

(54) DIFFUSE OPTICAL IMAGING CORRECTED FOR BOUNDARY EFFECTS

(75) Inventors: Frédéric Leblond, West Lebanon, NH (US); Simon Fortier, Châteauguay (CA)

(73) Assignee: ART, Advanced Research Technologies Inc., Ville-Saint-Laurent (CA)

( * ) Notice: Subject to any disclaimer, the term of this patent is extended or adjusted under 35 U.S.C. 154(b) by 1241 days.

(21) Appl. No.: 12/016,678

(22) Filed: Jan. 18, 2008

(65) Prior Publication Data

US 2009/0080723 A1    Mar. 26, 2009

Related U.S. Application Data

(60) Provisional application No. 60/885,872, filed on Jan. 19, 2007.

(51) Int. Cl.
*G01B 11/24* (2006.01)
(52) U.S. Cl. .................................................. 356/601
(58) Field of Classification Search ........... 356/601–624
See application file for complete search history.

(56) References Cited

U.S. PATENT DOCUMENTS

2006/0285002 A1* 12/2006 Robinson et al. ............. 348/335

OTHER PUBLICATIONS

Contini et al., Photon migration through a turbid slab described by a model based on diffusion approximation. I. Theory, Optical Society of America, Jul. 1, 1997, vol. 36, No. 19, pp. 4587-4599.

* cited by examiner

*Primary Examiner* — Tarifur Chowdhury
*Assistant Examiner* — Tara S Pajoohi
(74) *Attorney, Agent, or Firm* — McCarter & English LLP (57) ABSTRACT

A method of optically imaging an object includes the determination of a source point and a destination point within the object. Planar boundaries are selected that approximate a geometrical shape of the object, and virtual sources are found using a reflection of the original source through the boundaries. Subsequent reflections of the added sources may be used to find higher order sources. Contributions to an optical transfer function from each of the added sources are added to determine a cumulative optical transfer function until a convergence limit is reached. The resulting optical transfer function is more accurate than the original in that it takes boundary phenomena into consideration.

15 Claims, 8 Drawing Sheets

DIFFUSE OPTICAL IMAGING CORRECTED FOR BOUNDARY EFFECTS

FIELD OF THE INVENTION

This application relates generally to the field of optical imaging and, more specifically, to optical imaging of objects the boundaries of which cannot be exactly represented by planes.

BACKGROUND OF THE INVENTION

The prevalence of near-infrared (NIR) imaging within the multi-disciplinary field of molecular imaging has grown in recent years. This type of imaging has intrinsic advantages (e.g., low cost, non-invasive) when compared to other modalities such as positron emission tomography, magnetic resonance imaging, and computed tomography. However, several challenges remain before fluorescence NIR tomography algorithms combined with a mono-modal clinical device can provide quantitatively reliable information.

SUMMARY OF THE INVENTION

In accordance with the present invention, a method is provided for optically imaging an object which involves the calculation of an optical transfer function both from an identified source location and from a plurality of virtual source locations, each found by reflecting sources through a set of boundaries that approximate the shape of the object. This optical transfer function may be used in computing, from one point to another in the object medium, quantities such as optical fluence or photon current. In the method, a plurality of planar boundaries are defined that approximate the object shape. These boundaries may be extrapolated boundaries that each have a finite distance, in a direction away from the object, from boundaries actually selected to approximate the general shape of the object. This finite distance may be a function of a refractive index difference between an interior of the object and an exterior of the object.

An original source point and a destination point within the object are defined. The source point may be a location within the object medium a distance $z_0$ from the object surface, $z_0$ being equal to $1/\mu_s'$ where $\mu_s'$ is a reduced scattering coefficient of a diffusive medium of the object, or it may be any location within or on the surface of the object. A first optical transfer function is then determined from the source point to the destination point. A virtual source is then located at a point having reflection symmetry to the source point relative to one of the planar boundaries. In essence, the original source is "reflected" through the boundary to locate the new source, which is equal in magnitude but opposite in sign to the original source. A second optical transfer function is then determined from the virtual source to the destination point, and the first optical transfer function and the second optical transfer function are combined to form a modified optical transfer function. During a measurement, optical data is collected that is indicative of a composition of the object medium present at the destination point, and image data is generated by processing the collected optical signal using the modified optical transfer function.

In the same manner that a first virtual source is determined, as described above, additional virtual sources may also be determined by reflecting the original source point through each of the boundaries. After the determination of each new virtual source, an optical transfer function contribution may be determined that is representative of the optical transfer function between the new virtual source point and the destination point. This optical transfer function contribution is then added to a cumulative optical transfer function that includes the contributions from the first optical source and each subsequently added source. After adding a predetermined number of contributions to the cumulative optical transfer function, the result may be compared to the previous cumulative optical transfer function and, if the relative difference is below a predetermined threshold, a decision may be made that no additional virtual sources are subsequently added.

By reflection of the original source through each of the boundaries, a set of virtual sources are determined that may be considered first order sources. The method of the present invention may also include the determination of second order sources, each found by reflecting a first order source through one of the boundaries. This process may be continued such that, for each added set of virtual sources (i.e., first order sources, second order sources, etc.), a new set of virtual sources may be found by reflecting the sources of the added set relative to the boundaries, the new set being of a next higher order relative to the previously added set of sources. Notably, if the reflection of any virtual source results in an new source that has the same location and the same sign as an existing source, no optical transfer function contribution is determined using that source, and that source is deemed to be "invalid." This prevents the reflection of a virtual source back onto a source from which it originated. In addition, if the reflection of a virtual source results in a new virtual source which is valid but which falls within the geometrical boundaries of the object, an optical transfer function contribution from that source may be omitted from the calculation. Moreover, the determination of such a source may be used as a basis for deciding to add no further virtual sources.

BRIEF DESCRIPTION OF THE DRAWINGS

Further features and advantages of the present invention will become apparent from the following detailed description, taken in combination with the appended drawings, in which.

DETAILED DESCRIPTION

Optical fluorescence spectroscopy may be based on single photon emissions associated with a red-shifted transition from an excited electronic state to a lower state. The so-called Stokes shift between the peak of the absorption band and that of the fluorescence band is a measure of the relaxation process associated with non-radiative transitions occurring in the excited state. The relevant intrinsic physical properties of fluorescent molecules are the absorption cross-section ($\sigma$), the lifetime ($\tau$) and the quantum efficiency ($\phi$). The absorption cross-section is related to the fluorescent molecules number density ($N_T$), the molar extinction coefficient ($\epsilon_F$) and the molar concentration (C) through $\sigma = \epsilon_F C / N_T$. The decay of the fluorescence intensity is characterized by the sum of radiative and non-radiative decay rates ($\tau_r^{-1}$ and $\tau_{nr}^{-1}$). Finally, the quantum efficiency, $\phi = \tau_{nr}(\tau_{nr}^{-1} + \tau_r^{-1})$, is a measure of the number of photons emitted to the number of photons absorbed. The ideal situation for fluorescence imaging is when non-radiative contributions are absent ($\phi=1$). In the presence of a photon fluence source term $\Phi(r, t)$, which locally excites fluorophores, the typical single exponential decay is modified according to the time-dependent relation:

$$\frac{\partial N(\vec{r}, t)}{\partial t} = -\frac{N(\vec{r}, t)}{\tau} + \varphi \sigma \Phi(\vec{r}, t)[N_T(\vec{r}) - 2N(\vec{r}, t)] \quad (1)$$

where N represents the number density of excited fluorophores. In the limit where the quantum system of interest is non-saturated, i.e., the number of excited molecules is much less than the total number of fluorophores ($N \ll N_T$), the frequency domain solution to equation (1) is:

$$S(\vec{r}, \omega) = \frac{N(\vec{r}, \omega)}{\tau} = \frac{\varphi \varepsilon_F C(\vec{r})}{1 - i\omega \tau} \Phi(\vec{r}, \omega)$$

where S is a fluorescence source term representing the Fourier transform of a photon density per unit time.

One may make use of the injection of a collimated and coherent finite duration beam of NIR light into a biological tissue followed by photon detection at another spatial location. Typically, when propagating in biological tissues, photons are highly scattered. In terms of physical parameters this can be represented by a large ratio of the scattering over the absorption coefficient. This leads to rapid photon randomization once they have entered the medium and, as such, an incident laser pulse can be modeled as an isotropic source inserted some distance under the tissue surface. In order to correctly model light transport for arbitrary samples (taking into account variations in optical parameters, shape, size, etc.), full radiative transport theory should be considered. However, the complexity of the associated integro-differential equation (the "radiative transfer equation", or RTE) is such that the amount of computer processing time necessary to solve it is prohibitive for the development of commercial tomography algorithms. As a result, it is common in the field of diffuse optical imaging to consider the "diffusion approximation" (DA) to the RTE. The resulting equation is the so-called "time-dependent diffusion equation" (DE):

$$\frac{n}{c} \frac{\partial \Phi(\vec{r}, t)}{\partial t} - \vec{\nabla} \cdot D(\vec{r}) \vec{\nabla} \Phi(\vec{r}, t) + \mu_a(\vec{r}) \Phi(\vec{r}, t) = S(\vec{r}, t) \quad (2)$$

where $\Phi$ is the photon fluence, $\mu_a$ the absorption coefficient, $\mu_s'$ the reduced scattering coefficient, n the index of refraction, c the vacuum speed of light and S a source term. Strictly speaking, this equation can be used only if the following conditions are satisfied: (1) the source-collection point distance is large enough for full photon randomization to have occurred, (2) the reduced scattering to absorption ratio is large, (3) the index of refraction is constant throughout the medium, and (4) there are no non-scattering regions inside the medium.

Among the difficulties associated with small animal imaging is the uncertain validity of the DA for the relatively small volumes considered. While there exist methods for dealing with domains having different indices of refraction as well as with the presence of void regions, their application requires a priori knowledge, which is not available for the mono-modal type of imaging discussed herein. Moreover, the high variability of optical properties due to organs and tissues makes it questionable as to whether or not the DA is valid for all line-of-sights traced across the animal.

Figure 1:
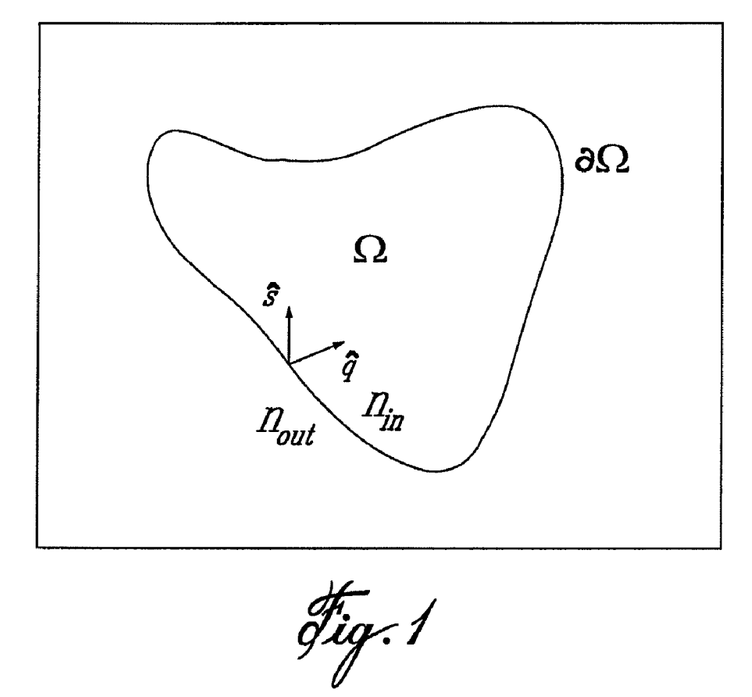
FIG. 1 is a schematic depiction of a turbid medium with domain $\Omega$ and boundary $\partial\Omega$.

Shown in FIG. 1 is a schematic view of a diffusing medium of arbitrary shape that is bounded by the surface $\partial \Omega$. Radiative energy moving in a direction s, per unit solid angle, per unit time, per unit area normal to the direction s is labeled I(r, t, s). This quantity is often referred to as the specific light intensity or radiance. The exact boundary condition for the diffuse specific intensity when there is no mismatch between the refractive index of the diffusing and of the surrounding medium is that there should be no diffused light entering the medium, i.e., $$I(\vec{r}, t, \hat{s}) = 0, \quad (2.1)$$

for s pointing inward and for r on the boundary $\partial \Omega$.

When taking the diffusion limit to the RTE it is assumed that the specific intensity is almost isotropic. Due to the simple angular distribution condition, (2.1) cannot be satisfied exactly and some approximate boundary condition must be devised. It is therefore possible to replace condition (2.1) with the condition that on surface $\partial \Omega$ the total diffuse flux inwardly directed should vanish, such that:

$$\int_{\hat{s} \cdot \hat{q} > 0} I(\vec{r}, t, \hat{s}) \hat{s} \cdot \hat{q} d\sigma = 0, \quad (2.2)$$

for r on $\partial \Omega$, where q is an inwardly directed unit vector normal to the boundary, as shown in FIG. 2.1.

Condition 2.2 is no longer valid when a refractive index mismatch exists at the boundary. In this case, the total diffuse flux at the boundary directed into the medium is the part of the outwardly directed flux reflected by the surface, and $$\int_{\hat{s} \cdot \hat{q} > 0} I(\vec{r}, t, \hat{s}) \hat{s} \cdot \hat{q} d\sigma = \int_{\hat{s} \cdot \hat{q} > 0} R(\hat{s}) I(\vec{r}, t, \hat{s}) |\hat{s} \cdot \hat{q}| d\sigma, \quad (2.3)$$

where R(s) is the Fresnel reflection coefficient for non-polarized light, $$R(\hat{s}) = \frac{1}{2} \left[ \left( \frac{n\cos(\theta_i) - \cos(\theta_t)}{n\cos(\theta_i) + \cos(\theta_t)} \right)^2 + \left( \frac{\cos(\theta_i) - n\cos(\theta_t)}{\cos(\theta_i) + n\cos(\theta_t)} \right)^2 \right] \quad (2.4)$$

In equation (2.4) $n = n_{in}/n_{out}$ characterizes the relative index mismatch at the boundary, $\theta_i$ is the angle of incidence of light, such that:

$$\cos(\theta_i) = -\hat{s} \cdot \hat{q},$$

and $\theta_t$ is the refracted angle, such that:

$$\theta_t = \arcsin(n \sin(\theta_i)).$$

The effect of this reflection is to induce a redistribution of light into the turbid medium. In terms of the fluence (average diffuse intensity) $\Phi(r, t)$ it can be shown, using Fick's law, that the boundary condition (2.3) becomes:

$$\Phi(\vec{r},t) - 2AD\hat{q}\cdot\nabla\Phi(\vec{r},t) = 0, \quad (2.5)$$

for r on $\partial\Omega$. The latter expression is referred to as the "partial current boundary condition." Exact analytic expressions for A (which is a unitless scaling function dependent on n) are known in the art, as are useful approximation expressions. Following this, for $n \leq 1$:

$$A = 3.084635 - 6.531194n + 8.357854n^2 - 5.082751n^3 + 1.171382n^4,$$

while for n>1 the expression becomes $$A = 504.332889 - 2641.00214n + 5923.699064n^2 - 7376.355814n^3 + 5507.53041n^4 - 2463.357945n^5 + 610.956547n^6 - 64.8047n^7$$

Notably, for most biological tissues an index of refraction corresponding to $n_{tissue}=1.4$ can be used.

Whenever there exists a tissue boundary a condition must be imposed there. Boundary condition (2.5) is difficult to implement directly for solutions to the diffusion equation. The "extrapolated boundary condition" is often used as a good approximation to the "partial current boundary condition." The extrapolated boundary condition assumes that the fluence vanishes exactly at an extrapolated boundary outside the turbid medium. It can be shown that the latter boundary should be located a distance $Z_e=2AD$ from the boundary outside the turbid medium. This approximation assumes linear behavior of the fluence around the geometrical boundaries. Herein, extrapolated boundary conditions are imposed.

The time-dependent diffusion equation with homogenous and isotropic optical properties may be written as:

$$\frac{1}{v}\frac{\partial \Phi(\vec{r},t)}{\partial t} - D\nabla^2 \Phi(\vec{r},t) + \mu_a \Phi(\vec{r},t) = S(\vec{r},t), \quad (2.7)$$

where the source term is assumed to be point-like of the form $$S(\vec{r},t) = N_0 \delta^{(3)}(\vec{r}-\vec{r}_s)\delta(t-t_0), \quad (2.8)$$

where $r_s$ and $t_0$ characterize the spatial and temporal location of the source. The corresponding solution with boundary condition 2.6 is $$\Phi(\vec{r}, t; \vec{r}_s, t_0) = \frac{N_0 v}{(4\pi Dv)^{3/2}(t-t_0)^{3/2}} \exp\left(\frac{|\vec{r}-\vec{r}_s|^2}{4Dv(t-t_0)} + \mu_a v(t-t_0)\right).$$

One can also show that the frequency domain equivalent of 2.7 is $$\nabla^2 \Phi^X(\vec{r}, \omega) + k_X^2 \Phi^X(\vec{r}, \omega) = -\frac{N_0}{\sqrt{2\pi}\, D^X}\delta^{(3)}(\vec{r}-\vec{r}_s),$$

with solutions of the form $$\Phi^X(\vec{r}, \omega; \vec{r}_s) = \frac{N_0}{\sqrt{2\pi}}\frac{1}{4\pi D^X}\frac{e^{ik_X|\vec{r}-\vec{r}_s|}}{|\vec{r}-\vec{r}_s|}.$$

For any simple geometry the "method of images" is a known way that can be used to write down solutions to the diffusion equation.

Figure 2:
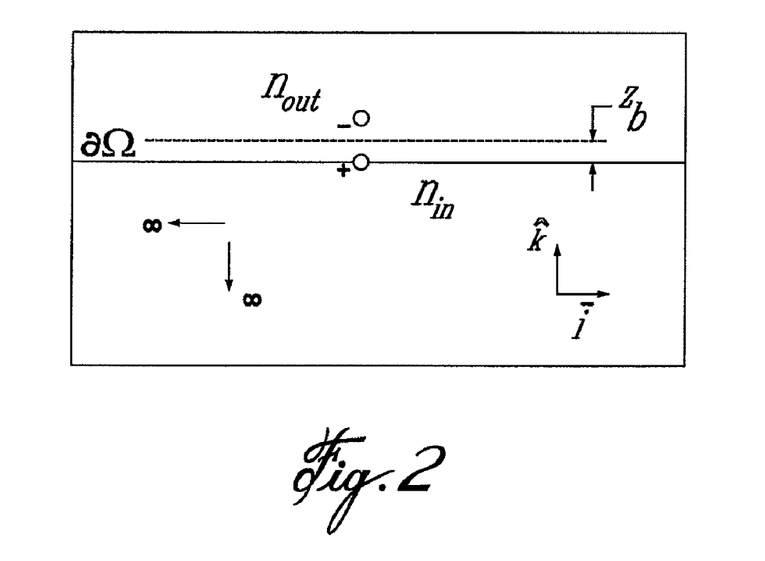
FIG. 2 is a schematic depiction of an infinite medium with a source inserted on its boundary as an example of source placement for the present invention.

A simple example of an extrapolated boundary condition makes use of a semi-infinite medium as depicted in FIG. 2. A delta-function source as described above in equation (2.8) is assumed to lie on the surface $\partial\Omega$, an infinite two-dimensional plane. In order to satisfy the extrapolated boundary condition the fluence must vanish on the outer extrapolated boundary (shown in the figure as dotted line 14). This is accomplished by inserting a source of negative sign a distance $2z_b$ away from $\partial\Omega$ in a direction normal to the boundary. The corresponding time domain and frequency domain solutions are thus, respectively, $$\Phi_{\frac{1}{2}\infty}(\vec{r}, t) = \Phi(\vec{r}, t; \vec{r}_+, t_0) - \Phi(\vec{r}, t; \vec{r}_-, t_0), \text{ and}$$

$$\Phi_{\frac{1}{2}\infty}(\vec{r}, \omega) = \Phi(\vec{r}, \omega; \vec{r}_+) - \Phi(\vec{r}, \omega; \vec{r}_-),$$

where $r^+$ is the vector locating the laser source on $\partial\Omega$ while $r^-$ pertains to its image. Assuming the origin O to be at the location of the source 12 indicated in FIG. 2, one finds $$\vec{r}_+ = (\vec{0}, 0), \text{ and}$$

$$\vec{r}_- = (\vec{0}, +2z_b).$$

Thus, as shown in the figure, a positive source is located at the origin and a negative source located an equal distance from the extrapolated boundary to its opposite side.

The diffusion equation deals with incoherent, un-polarized and randomized photons. However the laser source inserted on the boundary is a focused beam of coherent photons. It is therefore necessary to effectively insert the source one mean free path $z_0$ below the surface $\partial\Omega$, i.e., $$\vec{z}_0 = -\frac{1}{\mu'_s}\vec{k}.$$

Therefore whenever there is a planar boundary the sources should be translated as follows (again assuming the origin to be located as indicated on FIG. 2):

$$\vec{r}_{+,m} = (\vec{0}, -z_0),$$

$$\vec{r}_{-,m} = (\vec{0}, 2z_b+z_0).$$

This translated location of the sources is omitted from FIG. 2 for clarity. However, those skilled in the art will recognize that the two sources retain their symmetrical positioning about the extrapolated boundary relative to each other.

Figure 3:
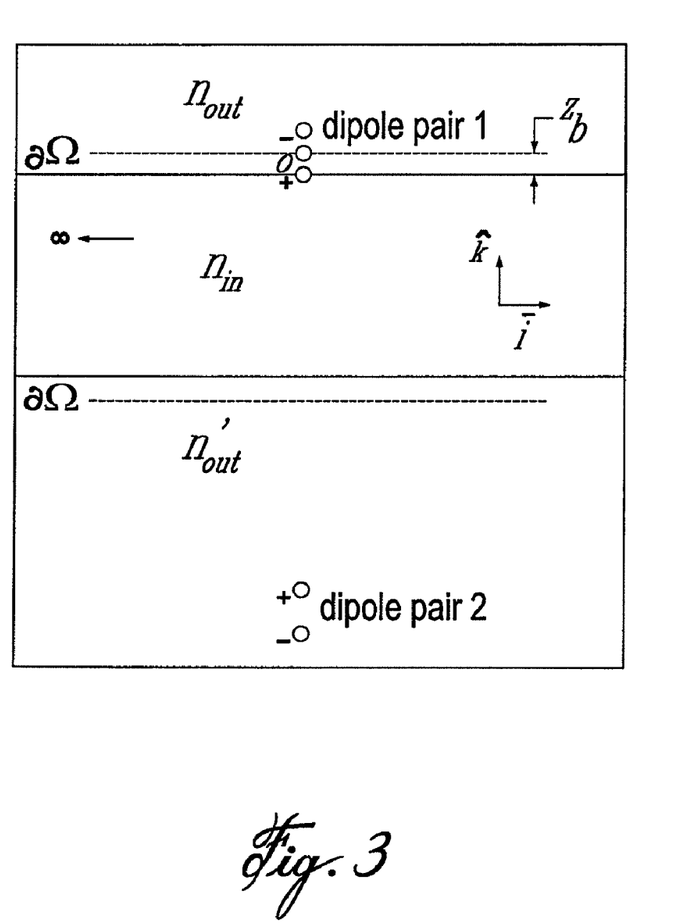
FIG. 3 is a schematic depiction of an infinite slab with a source inserted on the boundary.

The example of FIG. 2 may be extended to a slightly more complicated geometry, i.e., that of a slab, as shown in FIG. 3. This example is generalized to the case where there are two different exterior indices of refraction: $n_{out}$ and $n'_{out}$. The solutions can be written as:

$$\Phi_{slab}(\vec{r}, t) = \sum_{m=-\infty}^{+\infty} [\Phi(\vec{r}, t; \vec{r}_{+,m}, t_0) - \Phi(\vec{r}, t; \vec{r}_{-,m}, t_0)], \text{ and}$$

-continued $$\Phi_{slab}(\vec{r}, \omega) = \sum_{m=-\infty}^{+\infty} [\Phi(\vec{r}, \omega; \vec{r}_{+,m}) - \Phi(\vec{r}, \omega; \vec{r}_{-,m})].$$

Assuming the origin of coordinates to be located at the source location before translation by $z_0$ (as shown in FIG. 3), it may be found that:

$$\vec{r}_{+,m} = (\vec{0}, -2m(s+2z_b) - z_0) \quad |m| \text{ even (including 0)}$$

$$\vec{r}_{+,m} = (\vec{0}, -2m(s+2z'_b) - z_0) \quad |m| \text{ odd}$$

$$\vec{r}_{-,m} = (\vec{0}, -2m(s+2z_b) + 2z_b + z_0) \quad |m| \text{ even (including 0)}$$

$$\vec{r}_{+,m} = (\vec{0}, -2m(s+2z'_b) + 2z'_b + z_0) \quad |m| \text{ odd}.$$

In the example of FIG. 3, the source is shown located on the surface of the slab, rather than offset toward the interior by $z_0$. Those skilled in the art will understand that the source may actually be so located in certain situations, but that it is more often located based on the $z_0$ offset. In addition, the different refractive indices outside of the medium (i.e., $n'_{in}$ and $n'_{out}$) make it desirable to use extrapolated boundaries that are located different relative distances from their corresponding real surfaces. However, it is important to note that the present invention is not based on boundaries between regions of differing refractive index but, rather, on boundaries between diffusive and non-diffusive media, as once a photon exits a diffusive medium it is lost.

Figure 4:
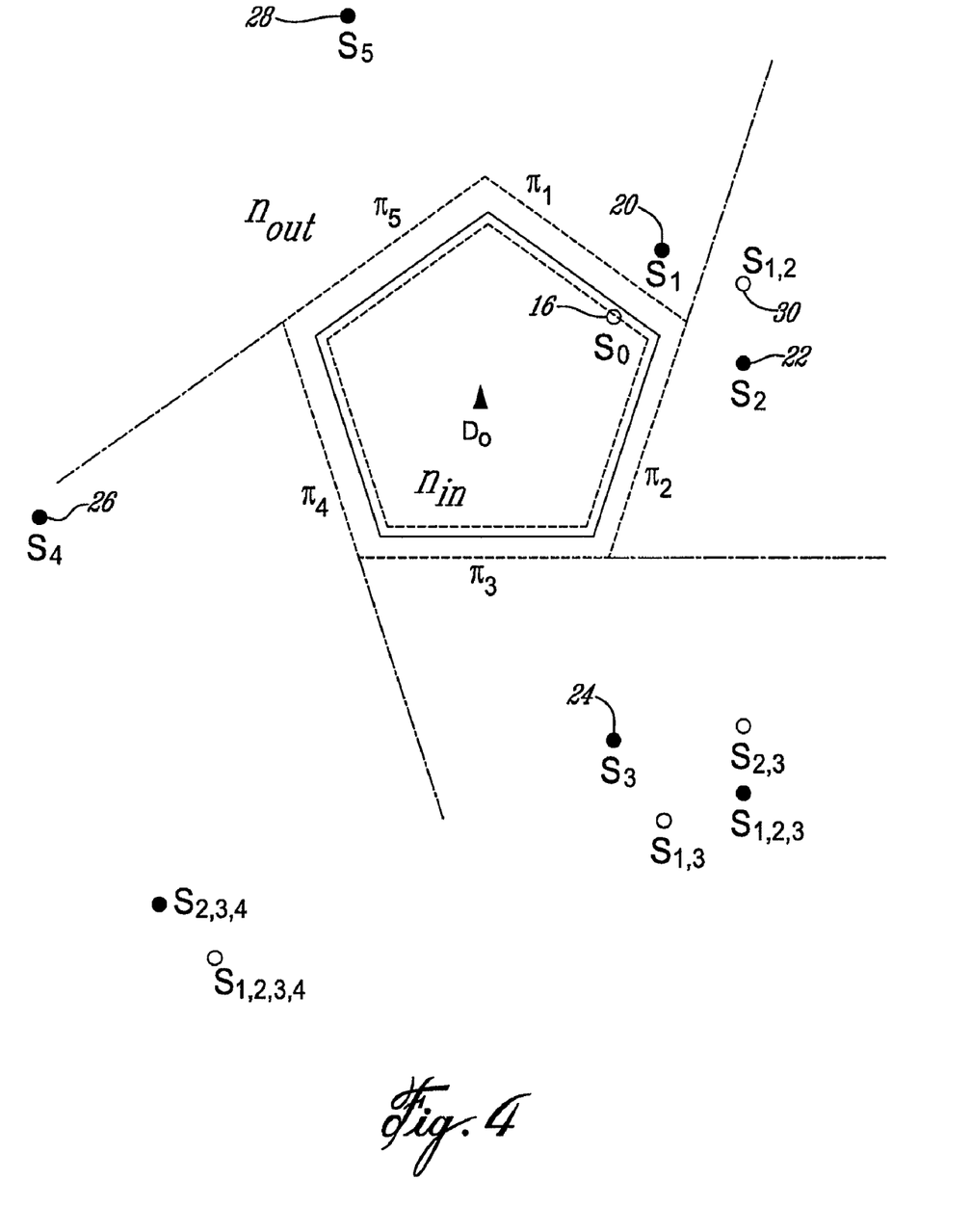
FIG. 4 is a schematic depiction of a random object geometry with multiple planar boundaries as may be used with the present invention.

The method of the present invention involves calculating homogeneous propagators for convex geometries that can be approximated as a finite number of two-dimensional surfaces separating a diffusive medium from its non-diffusive surroundings. FIG. 4 shows a sample geometry for demonstrating how the method may be used. In this figure, the different boundaries are shown in only two dimensions, but those skilled in the art will recognize that the method is intended for planes selected for three-dimensional objects.

Herein, much of the invention is described with regard to optical fluence, and the determination of a cumulative optical fluence value based on the contribution of a plurality of virtual sources which model boundary effects. However, those skilled in the art will understand that the present invention applies equally to other principles, such as photon current, in that the invention leads to the generation of a more accurate optical transfer function which may be used for different types of optical imaging.

Shown in the figure is a source $s_0$ 16 located at a position that is selected based on the location of the actual light source. Thus, if a laser is focused on the object from a point outside of the sample, the source 16 represents a location at which light from the laser is incident. The source 16 is also positioned a distance $z_0$ within the actual surface of the object for the reasons discussed above. For the purposes of this description, the source 16 is referred to as the "original" source, and may be labeled in terms of its polarity. This source represents the point of departure for the light on which this step of the fluence measurement depends when determining the fluence from the source to a destination of interest.

The present invention improves the fluence calculation by taking into account the effect of boundaries that separate the diffuse medium of the object from an external, non-diffuse medium (e.g., air). The selection of planes provide a rough model of the object, and may be used in the fluence determination. To determine the fluence from source 16 to a destination location $D_0$ 18 within the object, the radiative transfer equation may be applied. In the present invention, however, the fluence calculation is modified to take into account an approximated effect of the object boundaries. This is done by including virtual sources in the computation that are located based on the positions of the object boundaries.

After the selection of planes approximating the object boundaries, extrapolated boundaries are identified that each correspond to one of the planes, as discussed above with regard to simpler geometries. In FIG. 4, five extrapolated boundaries have been selected to correspond to the five planes approximating the object, and the extrapolated boundaries are labeled $\pi_1$, $\pi_2$, $\pi_3$, $\pi_4$ and $\pi_5$, respectively. Once an initial calculation of fluence is made using the source position 16 and destination position 18, the source 16 is "reflected" through each of the extrapolated boundaries in a consecutive manner, a new contribution being added to the fluence determination after each reflection. The "reflected" sources are of an opposite polarity than the original, as discussed above. Thus, a reflection of the original source so through boundary $\pi_1$ gives a negative source 20 located in a position having a reflection symmetry to original source 16 relative to the extrapolated boundary $\pi_1$. This source is labeled as $s_1$ in FIG. 4 to indicate that it results from the reflection of the original source through the boundary $\pi_1$. At this point, a new fluence calculation is made to determine the fluence from source 20 to destination point 18, and the result is added to the original fluence determination, thereby giving a cumulative fluence value.

Following a first reflection of the original source, a second reflection of the original source is performed, this time relative to boundary $\pi_2$. This reflection produces negative source 22, labeled $s_2$ to indicate that it is the reflection of the original source through the second boundary $\pi_2$. The fluence from this negative source is then added to the cumulative fluence value. After sources have been generated from reflection of the original source through each of the extrapolated boundaries (in this example, sources $s_1$, $s_2$, $s_3$, $s_4$ and $s_5$), the cumulative fluence is compared to the cumulative fluence following the determination of sources of a previous order, in this case the initial fluence computation. If the variation in the cumulative fluence with respect to the cumulative fluence at the end of the preceding reflection order has not fallen below the predetermined threshold, the process may thereafter continue with secondary reflections of the virtual sources found via the primary reflections.

Secondary reflections are the reflections of the "first order" virtual sources (e.g., $s_1$, $s_2$, $s_3$, $s_4$ and $s_5$), which were found by reflecting the original source directly. Each of these "second order" virtual sources is found by reflecting one of the first order sources through one of the extrapolated boundaries. For example, each of the sources $s_2$, $s_3$, $s_4$ and $s_5$ is reflected through the boundary $\pi_1$ (the source $s_1$ being omitted from this step, as it would reflect back on the original source). Similar reflections are performed for each of the other boundaries to find similar sets of secondary sources. Some of these secondary sources are shown in FIG. 4, such as secondary source 30, which is found by reflecting the first order source $s_1$ through the extrapolated boundary $\pi_2$. This second order source is a positive source (being the reflection of a negative source), and is labeled $s_{1,2}$ to indicate that it is the reflection of the source $s_1$ through the boundary $\pi_2$. Those skilled in the art will understand that the reflection of the first order sources will not include a reflection through the boundary that led to the original determination of that source. Thus, for example, there is no reflection of source $s_2$ through boundary $\pi_2$, since this would designate the location of the original source.

After each of the secondary sources is determined, a fluence calculation is made from that source to the destination point, and the resulting fluence contribution is added to the cumulative fluence value. If, at the end of adding all the secondary sources, the variation over that order of the cumulative value remains below the predetermined threshold, the process continues with a subsequent tertiary reflection, e.g, the reflection of $s_{1,2}$ through the boundary $\pi_3$ to locate source $s_{1,2,3}$. If, after the reflection of each of the second order sources through each of their non-originating boundaries, the threshold value for the variation in the cumulative fluence has not been reached, the process may continue to the location of fourth order sources. In this way, the present invention provides an iterative process toward a "convergence" in the fluence calculation, thereby improving the result by recognition of the effects produced by the approximated boundaries. For clarity, all of the second order reflections are not shown in FIG. 4. However, by way of example, second order source $s_{2,3}$ is shown. The figure also shows two third order sources: $s_{1,2,3}$, which is a reflection of source $s_{1,2}$ through boundary $\pi_3$; and $s_{2,3,4}$, which is a reflection of source $S_{2,3}$ through boundary $\pi_4$. In addition, one fourth order source, $s_{1,2,3,4}$, is shown which results from a reflection of source $s_{1,2,3}$ through boundary $\pi_4$.

As mentioned above, the iterative process uses threshold in the variation to the cumulative fluence calculation as a "stopping criterion." Thus, as the contributions from the reflected source determinations drop below a negligible value, the iterative process is terminated. However, a second stopping criterion may also be applied. In certain geometries the higher order source reflections may result in the location of a source within the interior of the object. Since the iterative process is based on the location of the virtual sources outside of the diffusive medium, this result may be prohibited. In such a case, the iterative process would be terminated when a source reflection was within the geometrical boundaries of the object, thus preventing a spurious result.

The method described above enables a determination of the fluence from the original source to the destination point. In one embodiment, the destination point my be located adjacent to a detection point, and the fluence calculation may be used to provide a characterization of the diffusive medium between the source and detection locations. In another embodiment, the destination point may be a point of interest within the object volume. For example, the destination point $D_1$ may be a location at which it is desirable to determine a characteristic, such as fluorophore concentration. In such a case, the determination of the fluence from source to destination point provides only part of the desired information, as it is also necessary to determine the fluence from the destination point to a detection point. Thus, a second calculation is done in which the destination point is taken as a source location, and a detection point is taken as the destination. This calculation follows the same steps as described above, using the diffusion equation and refining the result based on the additional contributions from virtual sources found using reflections through extrapolated boundaries. The overall process therefore uses the method of the present invention twice, once to determine the fluence from source to destination, and once to determine the fluence from destination to detector. Those skilled in the art will recognize that the basic method is the same for both steps, and that only the location of "source" and "destination" change.

Figure 5:
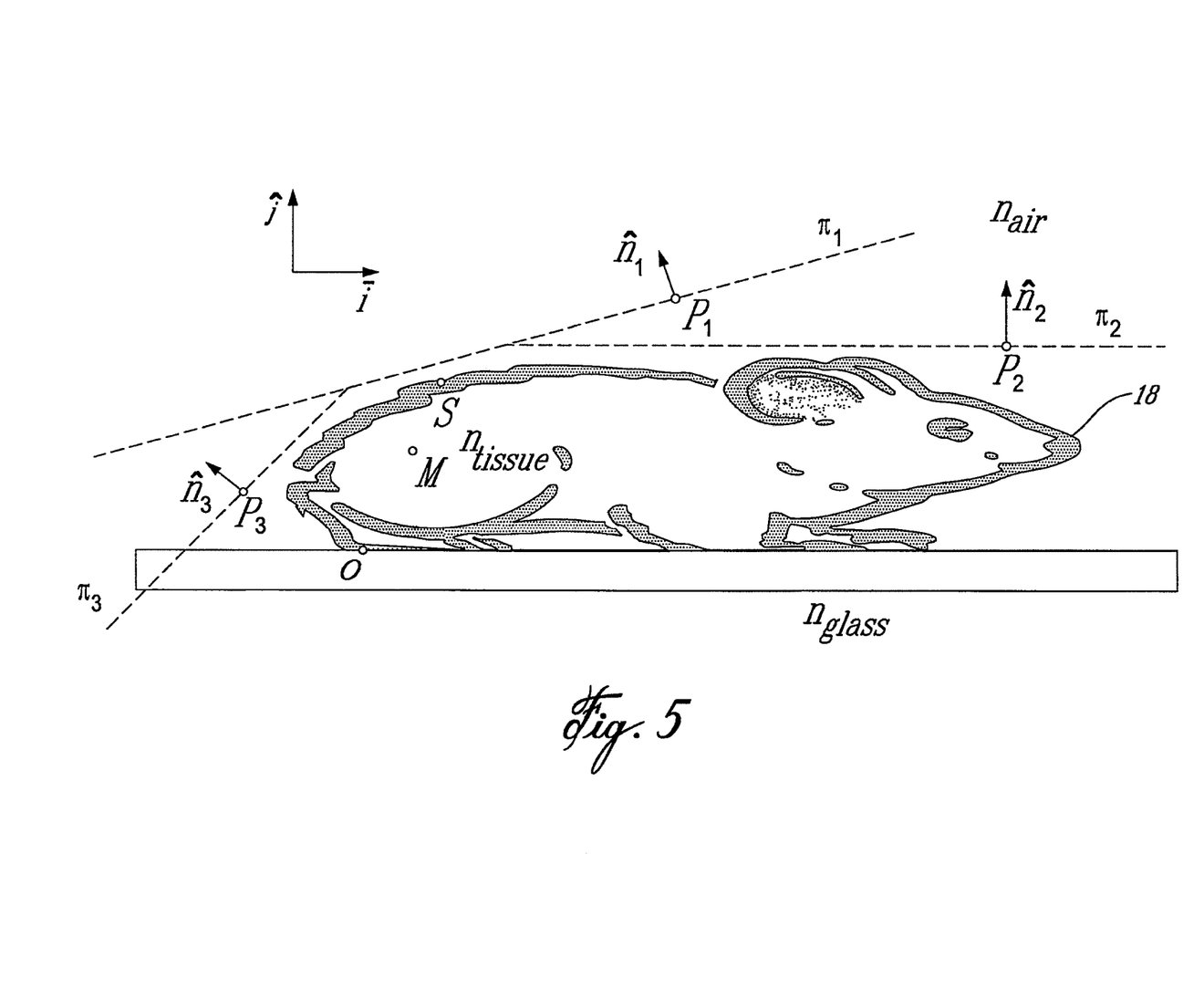
FIG. 5 is a schematic depiction of a mouse with boundaries overlaid to demonstrate the approximation of an object geometry.

An example of a turbid medium for imaging that has a complex shape is shown in FIG. 5. A small animal such as mouse 18 represents a typical imaging target due to its prevalent use in the medical research. Using the method of the present invention, a plane $\pi$ may be defined by a point P(r, s, t)$\in\pi$ and a normal unit vector $$\hat{n}=(a,b,c)\perp\pi.$$

This is shown in the figure for each of three planes $\pi_1$, $\pi_2$ and $\pi_3$, which represent three extrapolated boundaries based on selected surfaces. An origin O of $G_3$ (three-dimensional Cartesian coordinate system) may be defined as being any point located inside or on the boundary of the volume targeted for reconstruction. For example, it may be convenient to adopt the convention that the origin is always located at the lowest leftward corner of the voxels geometry, as is shown in FIG. 5.

The turbid medium is assumed to have an index of refraction $n_{in}$, while the exterior medium (i.e., outside of the turbid medium) has a refractive index $n_{out}$. For each boundary of the turbid medium there is an associated extrapolated boundary plane located a distance $z_b$ away within the exterior medium. If X(x,y,z) is the general point of $G_3$ then the plane $\pi$ is defined by the vector equation $$\hat{n}\cdot\overrightarrow{OX}=\hat{n}\cdot\overrightarrow{OP}.$$

Since the right-hand-side of this equation is a constant we set $$\hat{n}\cdot\overrightarrow{OP}=-h.$$

Therefore the characteristic equation for the plane $\pi$ becomes $$ax+by+cz=-h. \quad (2.9)$$

The definition of the planes associated with each planar boundary must be done in two steps. Firstly the unit vector normal to each plane must be found. Our basis assumption here is that we know the angles between the plane and the basis vectors i, j, k of $G_3$. These angles are respectively labeled $\alpha$, $\beta$ and $\gamma$. The angles between the normal vector n and these basis vectors are respectively $$\alpha',\beta',\gamma'.$$

Then the components of the unit vector n are simply $$a=\cos(\alpha'), b=\cos(\beta'), c=\cos(\gamma'),$$

i.e., the director cosines. Then the final step consists in choosing an arbitrary point P on each of the planes to complete the definition in order to evaluate h in equation 2.9. It should be clear that all coordinates must be evaluated with respect to the pre-defined origin O.

As discussed above, the elementary operation that needs to be performed repeatedly in the method is the finding of a reflection of a source (approximated by a geometrical point) across a plane $\pi$ (i.e., an extrapolated boundary). Given a source inserted at point Q, the coordinates of its reflection through $\pi$ (the reflection being labeled Q') are provided by the formula $$\overrightarrow{OQ'}=\overrightarrow{OQ}-2\vec{d}(Q,\pi),$$

where $\vec{d}$ represents the shortest displacement vector from plane $\pi$ towards point Q $$\vec{d}(Q,\pi)=(\hat{n}\cdot\overrightarrow{OQ}+h)\hat{n}.$$

FIG. 5 illustrates the procedure in the case of a mouse where three planes are chosen in order to find an approximated solution. The stopping criterion could be defined as $$\frac{\Phi^{(i+1)} - \Phi^{(i)}}{\Phi^{(i)}} < e.$$

The fluence $\Phi$ as defined in this document is not a directional quantity. In the diffusion limit it corresponds to the spherically symmetric contribution to the irradiance I. In this limit, the irradiance has a small directional component corresponding to the photon current that can be shown to take the form:

$$\vec{J} = -D\vec{\nabla}\Phi(\vec{r},t). \quad (2.10)$$

In certain cases, it may be desirable to relate this quantity rather than the fluence with an experimental signal. The operations of adding the contributions of sources and images and that of taking the derivative in 2.10 are commutative. This means that the techniques presented in this document for fluence calculations are directly extendable to instead considering the directional current.

The general steps of the method described above are depicted in the flowchart of FIGS. 6A and 6B. In step 602, an origin point and orthonormal basis for a coordinate system are defined by the user. Boundaries to approximate the object are then selected, and extrapolated boundaries are chosen, e.g., based on the diffractive index mismatch between the object and the regions outside of the object (step 604). The diffusion equation propagator is then evaluated between source point S and destination point D. First, in step 606, the $0^{th}$ order propagator G(0) is evaluated, that is, the diffusion equation is calculated using only the original source (as if there was an infinite medium). This original calculation is then modified by the subsequent iterative process.

Figure 6A:
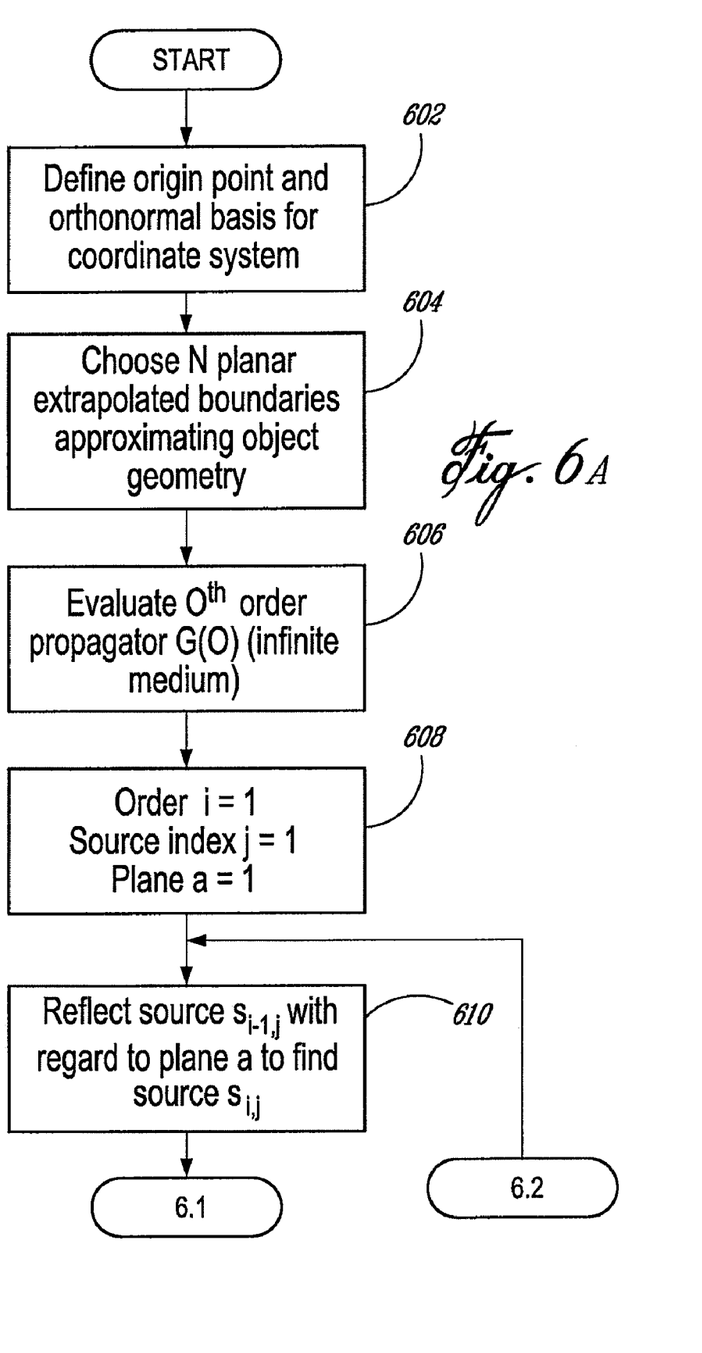
FIGS. 6A and 6B together depict a flow diagram showing the steps of a method according to the present invention.
Figure 6B:
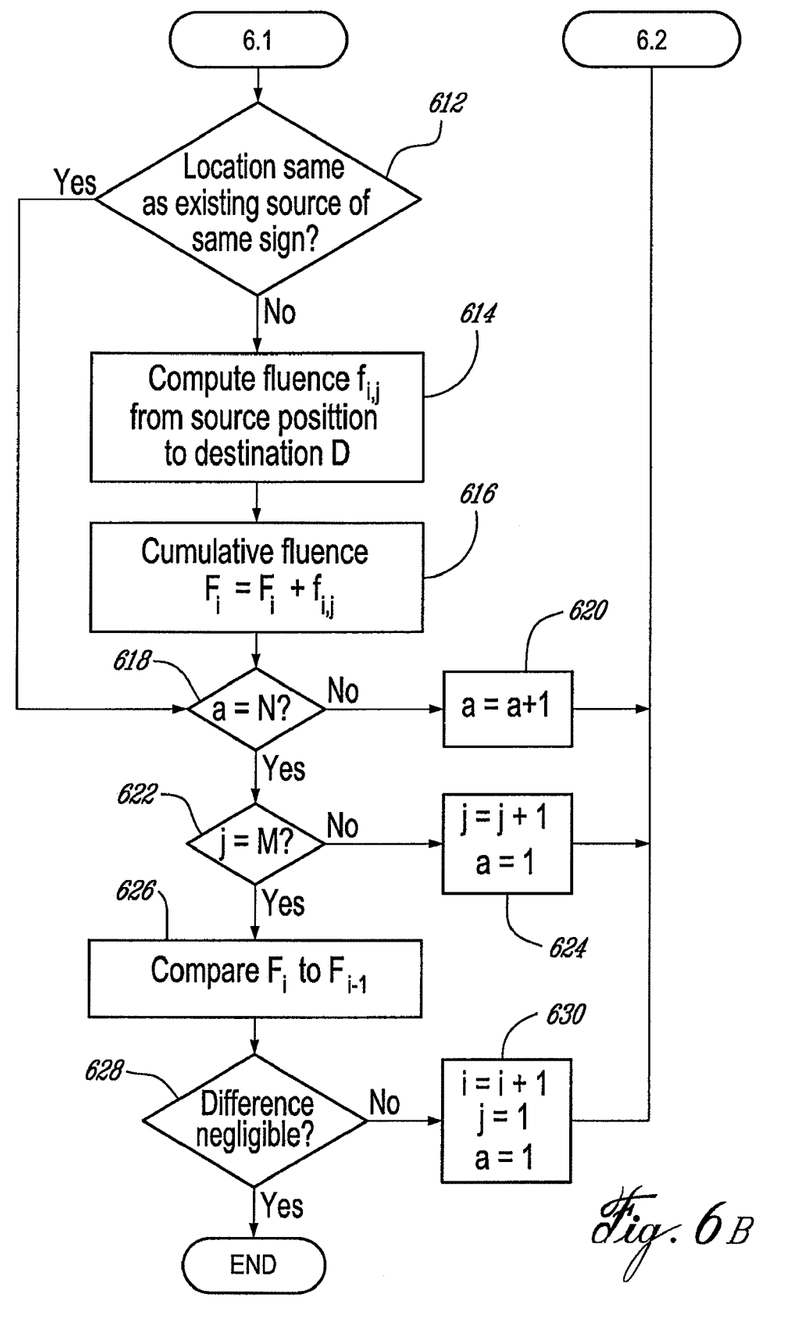
Figure 7A:
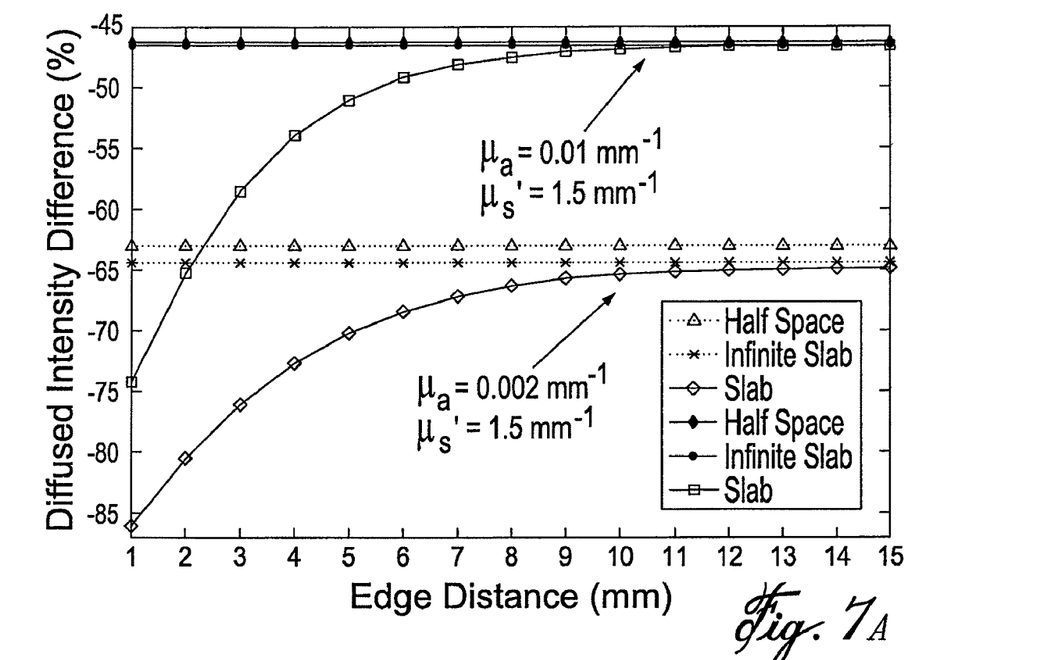
FIG. 7A is a chart depiction of diffused intensity difference (%) versus edge distance (mm)
Figure 7B:
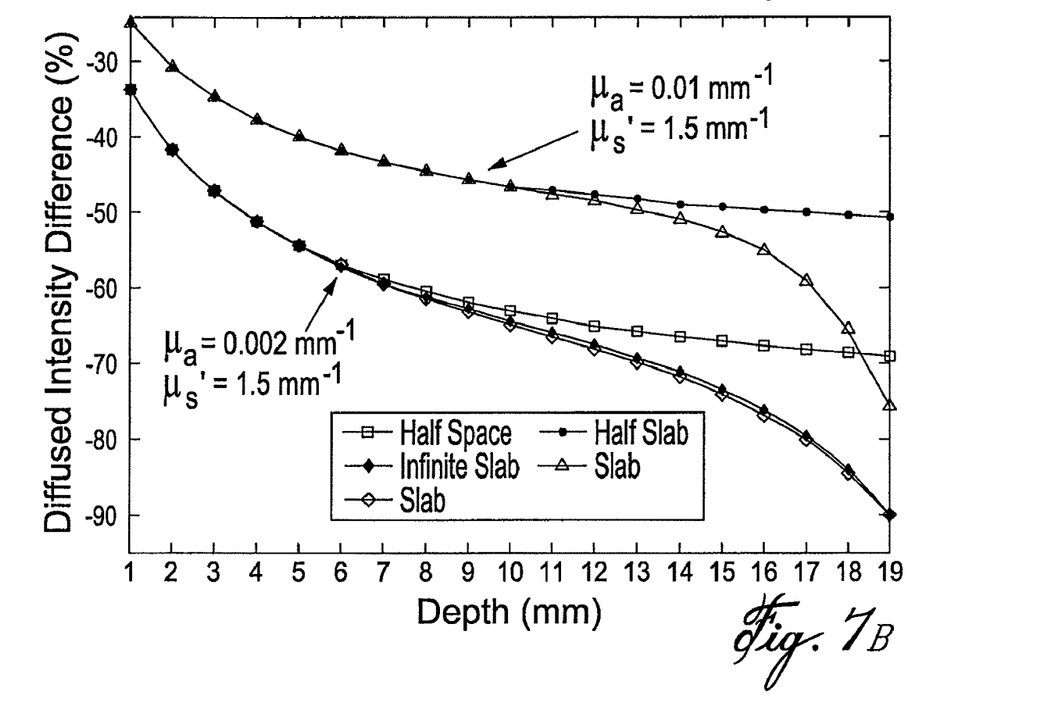
FIG. 7B is a chart depiction of diffused intensity difference (%) versus depth (mm)
Figure 7C:
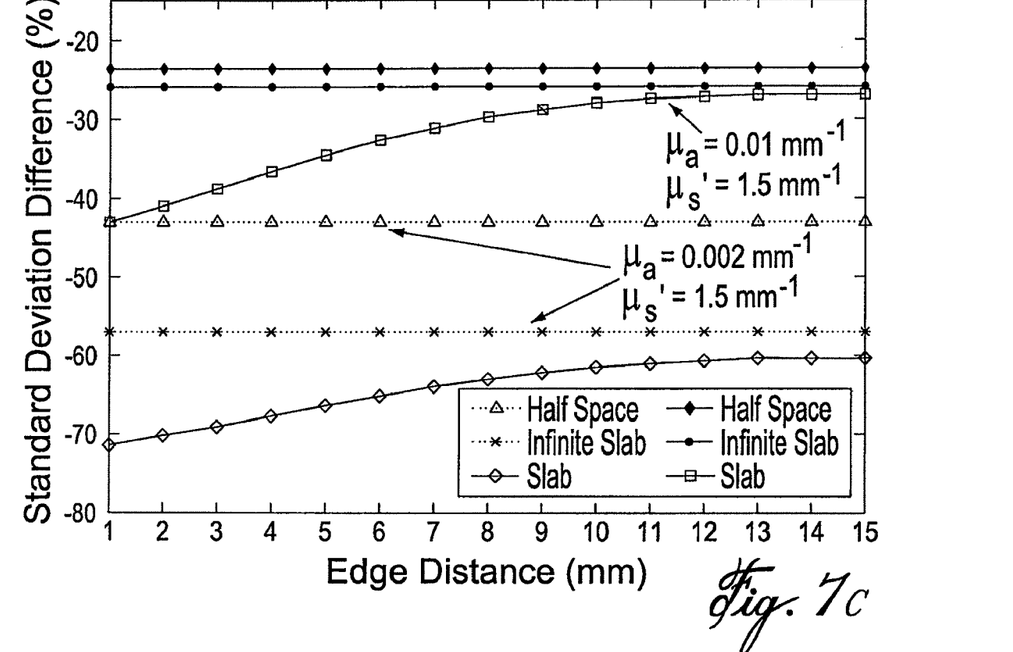
FIG. 7C is a chart depiction of standard deviation difference (%) versus edge distance (mm)
Figure 7D:
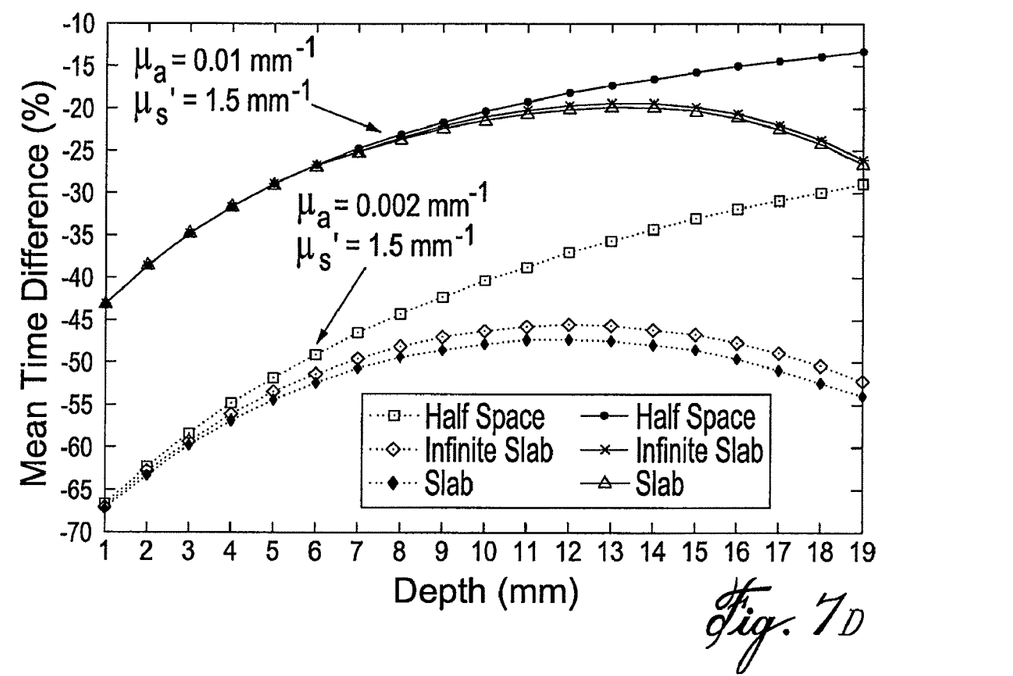
FIG. 7D is a chart depiction of mean time difference (%) versus depth (mm).

The higher order virtual sources are found using reflection of the original source or its images. Thus, as shown in step 608, the initial order i of the source to be reflected equals 1, and the process will involve finding sources for that current order. A source index j is used to represent which of the sources of the current order is being processed. The total number M of sources will be different for each order (for example, there is only one source for the $0^{th}$ order, while the second order will have a number of sources equal to the number of planes), and to start the process the source index j is set to one. The current plane a is also set to a value of 1.

In step 610, the current source for the previous order (indicated by the label $s_{i-1,j}$) is reflected with regard to the current plane a to find a new source $s_{i,j}$ of the current order (and opposite sign). To prevent the reflection back onto an originating source, the method includes checking to determine whether the source resulting from the reflection has the same location as an existing source with the same sign (step 612). If not, the fluence $f_{i,j}$ is computed from the position of the new source to the destination point D in step 614, and added to a cumulative fluence $F_i$ for the current order of sources (step 616). If, in step 612 the source found matches an existing source in both location and sign, this source is not added to the fluence computation, and the method instead skips directly to step 618.

In step 618, the value of a is tested to determine whether the source being reflected has been reflected through each of the planes and, if so, a is incremented in step 620 and the method returns to step 610 to continue with the next plane. If the final plane for the current order has been reached, the method determines whether all of the sources for the order have been reflected (step 622) and, if not, the source index is incremented to specify the next source, and a is reset to a value of 1 to begin the reflection of that source (step 624). If the final source of the order has be processed, as determined in step 620, the value of $F_i$ is compared in step 626 to the previously stored value for fluence, that being the value of $F_{i-1}$ determined during the processing of the previous order. This comparison is done to determine whether the difference in the overall fluence computation resulting from the processing of sources of a higher order has resulted in a non-negligible outcome. If the difference between the two is not negligible (i.e., above a predetermined threshold value) (step 628), the method continues with reflection of sources of the next order, that is, i is incremented, and j and a are reset to a value of 1 in step 630 before the method returns to step 610. If the difference is found to be negligible (i.e., equal to or below the predetermined threshold value), the method ends.

As discussed above, the method may also use as a stopping criterion the location of a reflected source within the interior of the object geometry. While this is not detailed in the method steps of FIGS. 6A and 6B, those skilled in the art will understand that the method may be easily modified to include this. Moreover, while the steps of the foregoing method are described in general with regard to the accompanying figures, these steps are guideline for the present invention, and not an exact algorithm for direct implementation.

While the invention has been shown and described with reference to a preferred embodiment thereof, it will be recognized by those skilled in the art that various changes in form and detail may be made herein without departing from the spirit and scope of the invention as defined by the appended claims. In particular, while much of the description is with regard to a determination of optical fluence, it will be understood that the invention is equally applicable to other quantities, such as photon current.

What is claimed is:

1. A method of optically imaging an object, the method comprising:
defining a plurality of planar boundaries that represent a geometrical shape of the object;
identifying an original source point and a destination point within the geometrical limits of the object;
determining a first optical transfer function from the source point to the destination point;
identifying a virtual source located at a point having reflection symmetry to the source point relative to one of the planar boundaries, the virtual source being equal in magnitude but opposite in sign to the original source;
determining a second optical transfer function from the virtual source to the destination point;
combining the first optical transfer function and the second optical transfer function to form a modified optical transfer function;
collecting optical data indicative of a composition of the object medium present at the destination point; and
generating image data by processing the collected optical data using the modified optical transfer function determination.

2. A method according to claim 1 further comprising choosing, as said boundaries, extrapolated boundaries that each have a finite distance, in a direction away from the object, from boundaries selected to approximate the geometrical shape of the object.

3. A method according to claim 2 wherein said distance between an approximating boundary and a corresponding extrapolated boundary is a function of a refractive index difference between an interior of the object and an exterior of the object.

4. A method according to claim 1 wherein the source point is located a distance $z_0$ away from a surface of the object toward the object interior, $z_0$ being equal to $1/\mu_s'$, where $\mu_s'$ is a reduced scattering coefficient of a diffusive medium within the object.

5. A method according to claim 1 wherein a plurality of virtual sources are determined, each being a reflection of the original source point through a different one of the boundaries.

6. A method according to claim 5 wherein a separate optical transfer function is determined for each of the virtual sources relative to the destination point.

7. A method according to claim 5 wherein, after the determination of each new virtual source, an optical transfer function contribution is determined that is representative of the optical transfer function between the new virtual source point and the destination point, and wherein the optical transfer function contribution is added to a cumulative optical transfer function that includes the first optical transfer function and each subsequently determined optical transfer function.

8. A method according to claim 7 wherein, after adding a predetermined number of optical transfer function contributions to the cumulative optical transfer function, the resulting cumulative optical transfer function is compared to a previous cumulative optical transfer function and, if the difference is below a predetermined threshold, no additional virtual sources are subsequently added.

9. A method according to claim 5 wherein the plurality of virtual sources determined as reflections of the original source are each first order sources, and wherein second order virtual sources are subsequently determined as reflections of first order sources relative to said boundaries.

10. A method according to claim 9 wherein, for each added set of virtual sources, a new set of virtual sources may be found by reflecting the sources of the added set relative to the boundaries, the new set of virtual sources being of a next higher order relative to the added set.

11. A method according to claim 10 wherein, if the location of an added virtual source is the same as the location of a previously determined source, and if the added virtual source has the same sign as the previously determined source, no optical transfer function contribution is determined using that source.

12. A method according to claim 9 wherein, after the determination of each new virtual source, a optical transfer function contribution is determined that is representative of the optical transfer function between the new virtual source point and the destination point, and wherein the optical transfer function contribution is added to a cumulative optical transfer function that includes the first optical transfer function and each subsequently determined optical transfer function.

13. A method according to claim 12 wherein, after adding the optical transfer function contribution to the cumulative optical transfer function, the resulting cumulative optical transfer function is compared to the previous cumulative optical transfer function and, if the difference is below a predetermined threshold, no additional virtual sources are subsequently added.

14. A method according to claim 13 wherein, if the location of an added virtual source is within the geometrical limits of the object, no optical transfer function contribution is determined using that source.

15. A method according to claim 14 wherein, if the location of an added virtual source is within the geometrical limits of the object, no additional virtual sources are subsequently added.

\* \* \* \* \*